United States Patent [19]

Boesten

[11] Patent Number: 5,306,826
[45] Date of Patent: Apr. 26, 1994

[54] PROCESS FOR PREPARATION OF AN OPTICALLY ACTIVE AMINO ACID AMIDE

[75] Inventor: Wilhelmus H. J. Boesten, Sittard, Netherlands

[73] Assignee: Stamicarbon B.V., Netherlands

[21] Appl. No.: 655,623

[22] Filed: Feb. 15, 1991

[30] Foreign Application Priority Data

Feb. 16, 1990 [NL] Netherlands ..................... 9000386

[51] Int. Cl.$^5$ ........................................... C07C 231/20
[52] U.S. Cl. ................................... 548/534; 562/401; 562/402; 564/164; 564/165; 564/198; 564/303; 564/424; 564/425
[58] Field of Search ............... 564/424, 425, 164, 165, 564/198; 548/532, 537, 534

[56] References Cited

U.S. PATENT DOCUMENTS

| | | | |
|---|---|---|---|
| 3,976,680 | 8/1976 | Clark et al. | 260/471 A |
| 4,072,698 | 2/1978 | Hylton et al. | 558/354 |
| 4,093,653 | 6/1978 | Boesten | 260/558 A |
| 4,275,217 | 6/1981 | Duhamel et al. | 548/344 |
| 4,285,884 | 8/1981 | Dannenberg et al. | 562/401 X |

FOREIGN PATENT DOCUMENTS

0001821 10/1978 European Pat. Off. .
0007834 7/1979 European Pat. Off. .

OTHER PUBLICATIONS

Jacques, et al., Enantiomers, Racemates, and Resolutions; Chapter 6, pp. 369–377. (no date given nor can one be found).

Noller, "Chemistry of Organic Compounds", (1965), 3rd Ed., p. 439.

*Primary Examiner*—Joseph Paul Brust
*Attorney, Agent, or Firm*—Cushman, Darby & Cushman

[57] ABSTRACT

The present invention relates to a process for the preparation of optically active amino acid amide. L-amino and D-amino acid amides are mixed in the presence of 0.5–4 equivalents of an aldehyde, relative to the quantity of amino acid amide, in the presence of a solvent and water. The mixture is converted in whole or in part by means of an optically active carboxylic acid into a salt of the amino acid amide and the carboxylic acid. A portion mainly consisting of one of the diastereoisomers of that salt is separated from the reaction mixture obtained. Instead of a mixture of L-amino and D-amino acid amides, it is also possible to use a mixture of the Schiff bases of an amino acid amide and an aldehyde, in which case it is not necessary to add extra aldehyde, and the required quantity of water amounts to at least 1 equivalent relative to the quantity of Schiff base. With this process, a high yield of optically active amino acid amide or the corresponding amino acid is rapidly obtained.

26 Claims, No Drawings

PROCESS FOR PREPARATION OF AN OPTICALLY ACTIVE AMINO ACID AMIDE

BACKGROUND OF THE INVENTION

1. Technical Field

The invention relates to a process for the preparation of optically active amino acid amide whereby a mixture of L-amino and D-amino acid amides, in the presence of an aldehyde and a suitable solvent, is converted in whole or in part, by means of an optically active carboxylic acid, into the salt of the amino acid amide and the carboxylic acid. A portion mainly consisting of one of the diastereoisomers of that salt is then separated from the reaction mixture obtained.

2. Background Information

A related process—an asymmetric transformation, as described for instance in 'Enantiomers, Racemates and Resolutions', Jean Jacques, André Collet, Samuel H. Wilen; John Wiley & Sons, New York (1981), pp. 369 ff.—is known from U.S. Pat. No. 4072698. In particular, this patent describes a process whereby optically pure nitriles, amides or Schiff bases of nitriles or amides, are prepared with an optically active acid in the presence of a ketone or an aldehyde. That publication is notably aimed at the preparation of optically pure nitriles, in particular 2-amino-2-(optionally p-substituted) phenyl acetonitrile, using optically pure tartaric acid and a ketone.

The yield of salt of nitrile and tartaric acid in the examples described in U.S. Pat. No. 4072698 is relatively low, i.e. not higher than 85%. With respect to amino acid amides and Schiff bases, no experimental data are mentioned, nor are claims made for processes utilizing such compounds as starting material

SUMMARY OF THE INVENTION

The present invention aims to provide a process in which optically active amino acid amide can be obtained in a high yield.

In one embodiment of the invention, L-amino and D-amino acid amides are mixed with an aldehyde and water in the presence of a solvent. An optically active carboxylic acid is also added to the mixture; thus, the mixture is converted, in whole or in part, into the salt of the amino acid amide and the carboxylic acid. A fraction or portion of the mixture consisting essentially of one of the diasteriomers of the salt is then separated out.

In another embodiment of the invention, Schiff bases of the L-amino and D-amino acid amides are mixed with water, a solvent and optically active carboxylic acid. The addition of aldehyde is not required. Again, the mixture is converted into the salt of the amino acid amid and the carboxylic acid. The above separation step is then carried out. In either of the two processes, water can be added at any stage of the reaction.

All U.S. patents and publications referred to herein are hereby incorporated by reference.

DETAILED DESCRIPTION OF THE INVENTION

According to the invention, optically active amino acid amide is obtained by adding water to the reaction mixture and by utilizing a quantity of aldehyde amounting to 0.5–4 equivalents relative to the quantity of amino acid amide.

If an amino acid amide and an aldehyde are started from, poor efficiency rates are obtained provided no water is added to the reaction mixture. Although the invention is not bound to any theoretical explanation, it seems that due to the presence of water, fewer side reactions occur, so that the losses are lower. More specifically, it appears that the presence of water inhibits some side reactions by which the starting amide would be converted into a chemical compound, other than the desired optically active amino acid, and thus would be lost. The efficiency achieved, for instance, if no water is added to the reaction mixture, starting from p-hydroxyphenylglycine amide and benzaldehyde, is only 81.3%, while if 1 equivalent of water is added to the reaction mixture, an efficiency of 92.5% is obtained. Starting from phenylglycine amide and benzaldehyde, the efficiency achieved is 87.7% and 96.0%, respectively. This is surprising because it is to be expected a priori that the presence of water will have a negative effect on the efficiency, since the asymmetric transformation proceeds via the Schiff base, the formation of which is inhibited by the presence of water. After all, it is to be expected that the presence of water has a negative effect on the establishment of equilibrium in the formation of the Schiff base. Moreover, water enhances the solubility of the diastereoisomeric salt which is recovered in solid form; thus, a lower yield should be expected. An additional negative aspect of the addition of water is that in many cases a two-phase system is formed which is difficult to filter and wash.

Aldehydes that can be used in the process according to the invention are for instance aromatic aldehydes, such as benzaldehyde, anisaldehyde, o-, p-, or m-nitrobenzaldehyde, o-, p- or m-chlorobenzaldehyde or aliphatic aldehydes, such as isobutyraldehyde or isovaleraldehyde. The quantity of aldehyde to be added is 0.5–4.0 equivalents relative to the quantity of amino acid amide, preferably 1–2 equivalents.

Instead of a mixture of L-amino and D-amino acid amides and an aldehyde, the starting material can also be a mixture of the Schiff bases of L-amino and D-amino acid amides. In this case, it is not absolutely necessary to add an extra quantity of aldehyde In order to obtain an optimum yield of the diastereoisomeric salt of optically active amino acid amide and optically active carboxylic acid, at least an equimolar quantity of water relative to the quantity of Schiff base should be added. Application of less than an equimolar quantity of water results in a virtually proportional decrease in the yield. For instance, an efficiency of 99.0% is achieved when using 1.1 equivalents of water in the asymmetric transformation of the Schiff base of phenylglycine amide and benzaldehyde with optically active mandelic acid, as opposed to 45.7% when no water is added.

Since the addition of large quantities of water will in many cases lead to large quantities of dissolved diastereoisomeric salt, and thus to a decrease in the quantity of diastereoisomeric salt that can be recovered in solid form, the quantity of water added in practice will not be too great, for instance, less than 20 equivalents of water relative to the quantity of amino acid amide or the Schiff base thereof The optimum quantity of water to be used varies with the amino acid amide chosen and can be easily determined by a skilled person. In most cases, the quantity of water will be between 0.1 and 4 equivalents relative to amino acid amide or the Schiff base thereof, preferably between 0.5 and 3 equivalents.

It is of no importance whether the water is added at the beginning of the reaction or in the course of the conversion process. The water can be added in any desired manner, for instance, as diluent of the reactants or the solvent. Preferably, a sufficient quantity of water is added before contact occurs between the amide and the carboxylic acid.

U.S. Pat. No. 4093653 describes a process for the preparation of optically active phenylglycine amide whereby a mixture of L- and D-phenylglycine amide is treated with an optically active acid in the presence of ketones. The yield in this process is lower and the required reaction time longer than in the present invention.

Mixtures of D,L-amino acid amides can be obtained in a manner known per se, for instance, by reacting the corresponding ester with ammonia.

In the process according to the invention, optically active carboxylic acids are used. In general, the acid strength (pKa) will be 3 to 5. The quantity of optically active carboxylic acid used can be varied within wide limits and will in general be between 0.9 and 1.2 equivalents of carboxylic acid relative to amino acid amide. Preferably, an equivalent quantity of carboxylic acid is used.

An appropriate choice of the optically active carboxylic acid is determined by, among other things, the specific amino acid amide In particular, the melting point of the diastereoisomeric salts should be a sufficiently high, in order to enable separation to be effected by means of crystallization. In addition, there should be a sufficient difference in solubility between the diastereoisomeric salts in the relevant solvents More specifically, the separation of the diastereoisomeric salts is based on their difference in solubility (i.e., the one forming crystals and the other staying in solution) to a certain extent. The larger the difference in solubility, the better the separation. If there is only a small difference in solubility, the crystallization step should be repeated many times in order to obtain a sufficient separation of the two salts For a technically/economically advantageous solution, the crystal form may also play a role, in connection with ease of filtration and purification by means of a washing liquid. For phenylglycine amide and p-hydroxyphenylglycine amide, for instance, good results are obtained with mandelic acid and 2-pyrrolidone-5-carboxylic acid. Moreover, these optically active carboxylic acids can be easily and almost quantitatively recovered through extraction by means of, for instance, methyl-t-butyl ether, methylisobutyl ketone, ethyl acetate, butyl acetate, amyl alcohol or by means of ion exchangers. The use of optically active mandelic acid gives the best results as regards the recoverability of the acid and the crystal form obtained.

Depending on the starting materials chosen (i.e., the amide and the optically active carboxylic acid), diastereoisomeric salts are formed as intermediates in the reaction. Thus, the invention also relates to, for example, the following intermediate compounds: the LD salt of L-phenylglycine and D-mandelic acid, the DL salt of D-phenylglycine amide and L-mandelic acid, the LD salt of L-p-hydroxyphenylglycine amide and D-mandelic acid, the DL salt of D-p-hydroxyphenylglycine amide and L-mandelic acid, the LL salt of L-methionine amide and L-2-pyrrolidone-5-carboxylic acid, the DD salt of D-methionine amide and D-2-p-pyrrolidone-5-carboxylic acid, the LD salt of L-homophenylalanine amide and D-Z-aspartic acid, and the DL salt of D-homophenylalanine amide and D-Z-aspartic acid.

Suitable solvents for the asymmetric transformation are, for instance, hydrocarbons, such as cyclohexane, heptane and octane, aromatic hydrocarbons, such as toluene, xylene and benzene, ethers, such as methyl tertiary butyl ether, dioxane, tetrahydrofuran and anisole, esters, such as butyl acetate and ethyl acetate, ketones, such as acetone, butanone, methyl isobutyl ketone, carboxylic acids, aldehydes or mixtures of these substances. A solvent should be chosen which does not enter into irreversible chemical reactions with the amino acid amide, the optically active carboxylic acid or the aldehyde.

The pressure at which the process according to the invention is carried out is not critical and is for instance 0.01-1 MPa. The process is preferably carried out at atmospheric pressure. The temperature can be varied within wide limits and is in general 70°-120° C., preferably 75°-100° C. The reaction time is usually approximately 1-8 hours, preferably 1-4 hours.

The slurry concentration of the diastereoisomeric salts is about 5-30 wt. %, preferably 10-20 wt. %.

The optically active amino acid amide can be obtained from the separated diastereoisomeric salt by dissolving the salt in a mixture of water and a virtually equimolar quantity of mineral acid, such as hydrochloric acid, sulphuric acid, nitric acid or phosphoric acid, and extracting the optically active carboxylic acid by means of an extraction agent. Suitable extraction agents are for instance ethers, alcohols, ketones or esters, such as methyl tertiary butyl ether, methyl isobutyl ketone, ethyl acetate, butyl acetate or amyl alcohol.

The optically active amino acid amide obtained can be converted into the corresponding amino acid in a known manner by hydrolysis with an excess of diluted mineral acids, such as hydrochloric acid, sulphuric acid, nitric acid or phosphoric acid. The hydrolysis is carried out at approximately 60°-100° C., preferably at 85°-95° C.

Normally, the diastereoisomeric salt is separated from the reaction mixture before the hydrolysis and further processing. Good results are also obtained, however, if the hydrolysis is carried out before filtering off the diastereoisomeric salt.

The invention will now be elucidated by means of the following examples, without being restricted thereto. Each experiment is carried out in a nitrogen atmosphere.

The analysis method used is thin-layer chromatography (TLC), with: Merck 60 F 254 silicagel being used as carrier; UV (short wave) and ninidrine being used as detection methods The three TLC eluents and the proportions by volume in which they are used are:

A CHCl$_3$—CH$_3$OH—NH$_4$OH (25 wt. %)
  60      45       20
B sec. butanol-formic acid-water
  75      15       10
C n-butanol-acetic acid-ethyl acetate-water
  1      1       1       1

The selectivity (enantiomeric purity) is defined as follows:

$$\text{selectivity} = 50\% + \frac{50 \times [\alpha]_D^{20}}{\max. [\alpha]_D^{20}} \%$$

The maximum specific rotations of a number of amino acid amides and/or their salts are given in Greenstein and Winitz, vol. 2, pp. 1196–2000, as well as in Beilstein 14 III, p. 1189. The maximum specific rotations of some amino acid amides and/or their salts are also described in U.S. Pat. No. 4,847,412: D-phenylglycine amide.HCl: $-100.8°$ (c=0.8; water) D-methionine amide.HCl: $-18.2°$ (c=1.0; water) D-homophenylalanine amide.½ H$_2$SO$_4$: $-15.7°$ (c=1.0; water) L-phenylalanine amide.½ H$_2$SO$_4$: $+17.8°$ (c=1.0; water). From the [applicant's] present inventor's own observations, the maximum specific rotation of D-p-hydroxyphenylglycine amide is known: $-121.5°$ (c=1.0; 1.0 N acetic acid).

COMPARATIVE EXAMPLE A

In a reaction flask provided with a stirrer, a thermometer and a reflux cooler, 23.8 g (0.10 mole) D,L-N-benzylidene phenylglycine amide, 15.2 g (0.10 mole) L-mandelic acid and 200 ml toluene are stirred for 2.5 hours at a temperature of 86° C. After cooling to 30° C. (¼ hour), the salt of D-phenylglycine amide and L-mandelic acid (DL salt) is filtered and washed on the glass filter with 4×25 ml toluene. The yield of diastereoisomeric DL salt, after drying, amounts to 13.8 g which corresponds to an efficiency of 45.7%.

1.0 g of the diastereoisomeric DL salt thus obtained is suspended in 10 ml water, to which subsequently 10 ml 12 N hydrochloric acid is added with stirring. After filtration and washing with 4×10 ml acetone on the glass filter of the D-phenylglycine amide.HCl crystals formed, the specific rotation of the D-phenylglycine amide HCl salt obtained (yield=0.55 ; efficiency=88.7%): $[\alpha]^{20}_D = -99.5°$ (c=0.8; water). According to the literature (Beilstein, 14 III, p. 1189), the specific rotation of D-phenylglycine amide.HCl is: $[\alpha]^{20}_D = -100.8°$ (c=0.8; water).

EXAMPLE I

The procedure described in comparative experiment A is repeated, on the understanding that 2.0 g (0.11 mole) water is added to the mixture of D,L-N-benzylidene phenylglycine amide and L-mandelic acid.

Results

Yield of diastereoisomeric DL salt: 29.9 g (efficiency=99.0%).

Yield of D-phenylglycine amide.HCl: 0.55 g (efficiency=88.7%).

Specific rotation: $[\alpha]^{20}_D = -101.3°$ (c=0.8; water).

COMPARATIVE EXPERIMENT B

In a reaction flask provided with a stirrer, a thermometer and a reflux cooler, 23.8 g (0.10 mole) D,L-N-benzylidene phenylglycine amide, 12.9 g (0.10 mole) L-2-pyrrolidone-5-carboxylic acid, 235 ml toluene and 15 ml (0.15 mole) benzaldehyde are stirred for 2.5 hours at a temperature of 84° C.

After cooling to 25° C. (16 hour), the 10 resulting diastereoisomeric salt of L-phenylglycine amide and L-2-pyrrolidone-5-carboxylic acid (LL salt) is filtered and washed on the glass filter with 4×25 ml toluene The yield of filtered product after drying amounts to 12.8 g.

According to a thin-layer chromatographic analysis, the product obtained contains more than an equivalent quantity of L-2-pyrrolidone-5-carboxylic acid. 2.0 g of the diastereoisomeric LL salt is dissolved in 10 ml water, to which subsequently 10 ml 12 N hydrochloric acid is added. After filtration and washing on the glass filter of the resulting L-phenylglycine amide.HCl crystals with 4×10 ml acetone, the specific rotation of the L-phenylglycine amide.HCl obtained (yield=0.1 g; overall efficiency=7.5%) is: $[\alpha]^{20}_D = +102.5°$ (c=0.8; water). Literature value of L-phenylglycine amide.HCl (Beilstein, 14 III. p. 1189): $[\alpha]^{20}_D = +100.8°$ (c=0.8; water).

EXAMPLE II

The same procedure is carried out as described in comparative experiment B; however, stirring takes place for 2.5 hours at 84° C. in the presence of 2.7 g (0.15 mole) water. Results: Yield of diastereoisomeric LL salt: 25.4 g (efficiency=91.0%). Specific rotation of L-phenylglycine amide.HCl (yield=1.2 g; efficiency=89.8%): $[\alpha]^{20}_D = +99.8°$ (c=0.8; water).

EXAMPLE III

In a reaction flask provided with a stirrer, a thermometer and a reflux cooler, 15.0 g (0.10 mole) D,L-phenylglycine amide, 15.2 g (0.10 mole) D-mandelic acid, 230 ml toluene, 20 ml benzaldehyde and 1.8 g (0.10 mole) water are stirred for 2 hours at a temperature of 88° C.

After cooling to 20° C. (0.5 hour), the resulting diastereoisomeric salt of L-phenylglycine amide and D-mandelic acid (LD salt) is filtered and washed on the glass filter with 4×25 ml toluene. The yield of TLC pure LD salt after drying amounts to 29.3 g, which corresponds to an efficiency of 97.0%.

The specific rotation of the optically pure LD salt (recrystallization) amounts to: $[\alpha]^{20}_D = +4.0°$ (c=1.0; water). 1.0 g of the diastereoisomeric LD salt obtained is suspended in 10 ml water, to which subsequently 10 ml 12 N hydrochloric acid is added with stirring. After filtration and washing with 4×10 ml acetone on the glass filter of the L-phenylglycine amide.HCl crystal mass obtained, the specific rotation of the TLC pure L-phenylglycine amide.HCl salt obtained (yield=0.55 g; efficiency=88.7%) is: $[\alpha]^{20}_D = +101.7°$ (c=0.8; water). The LD salt (22.7 g=0.075 mole) is dissolved at 50° C. in a mixture of 40 ml water and 2.7 ml 96 wt. % sulphuric acid (0.05 mole) and, after extraction with 5×50 ml methyl-b-butyl ether (removal of D-mandelic acid), hydrolyzed to L-phenylglycine at a temperature of 90° C. by means of 10 ml 96 wt. % sulphuric acid (0.18 mole) with stirring for 3 hours. After neutralization of the sulphuric L-phenylglycine hydrolizate by means of 28 ml 25 wt. % ammonia to an acidity of pH=5 and cooling to 30° C., the L-phenylglycine thus obtained is filtered and then washed on the glass filter with 5×10 ml water.

The yield of L-phenylglycine after drying amounts to 10.5 g, which corresponds to an efficiency of 92.9%.

The specific rotation of the TLC pure L-phenylglycine is: $[\alpha]^{20}_D = +157.7°$ (c=1.6; 2.6 wt. % hydrochloric acid). Literature value of specific rotation of L-phenylglycine (Beilstein 14 III, p. 1188): $[\alpha]^{20}_D = +157.5°$ (c=1.6; 2.6 wt. % hydrochloric acid).

EXAMPLE IV

The same procedure is carried out as described in example III, but with use of L-mandelic acid instead of D-mandelic acid. Results: Specific rotation and yield values: Optically pure DL salt (recrystallization): $[\alpha]^{20}_D = -4.1°$ (c=1.0; water); 29.0 g (efficiency=96.3%) TLC pure D-phenylglycine am $[\alpha]^{20}_D = -101.9°$ (c=0.8; water); 0.55 g (efficiency=88.7%) TLC pure D-phenylglycine: $[\alpha]^{20}_D = -157.4°$ (c=1.6; 2.6 wt. % hydrochloric acid); 10.4 g (efficiency=92.0%).

EXAMPLE V

In a reaction flask provided with a stirrer, a thermometer and a reflux cooler, a suspension of 30.0 g (0.20 mole) D,L-phenylglycine amide, 32.0 g (0.21 mole) L-mandelic acid, 400 ml toluene, 40 ml benzaldehyde and 5.4 g (0.30 mole) water is stirred for 2 hours at a temperature of 85° C. After cooling to 60° C., the suspension is poured into a mixture of 120 ml Water and 8.0 ml 96 wt. % sulphuric acid (0.144 mole). After separation of the organic phase at 50° C., the acid aqueous phase is extracted at this temperature with 4×60 ml ethyl acetate (removal of L-mandelic acid).

After addition of 30 ml 96 wt. % sulphuric acid (0.54 mole), the sulphuric D-phenylglycine amide solution is hydrolized to D-phenylglycine with stirring for 4 hours at 85° C.

The yield of D-phenylglycine after, successively, neutralization to pH=4 by means of 85 ml 25 wt. % ammonia, cooling to 20° C., filtration, washing on the glass filter with 5×30 ml water and drying, amounts to 27.2 g, which corresponds to an efficiency of 90.0%.

The specific rotation of the TLC pure D-phenylglycine is: $[\alpha]^{20}_D = -153.4°$ (c=1.6; 2.6 wt. % hydrochloric acid)

EXAMPLES VI-XI

D,L-phenylglycine amide is contacted with 1 equivalent optically active D-mandelic acid and the TLC pure L-phenylglycine amide.HCl salt, recovered as in example III, the quantities of aldehyde and water added being varied. The results are given in table 1, which also shows the temperature (T) in ° C. and the retention time (t).

COMPARATIVE EXPERIMENT C

A procedure analogous to example III is carried out up to the recovery of the TLC pure L-phenylglycine amide.HCl salt, but without addition of water, which results in a lower yield. The results and specific conditions are given in table 1.

COMPARATIVE EXPERIMENT D

A procedure analogous to example III is carried out up to the recovery of the TLC pure L-phenylglycine amide.HCl salt, but with only 0.1 equivalent benzaldehyde, which results in a very low selectivity. The results and specific conditions are given in table 1.

TABLE 1

| example | solvent | aldehyde (eq.) | water (eq.) | slurry concentr. | T | t | efficiency | selectivity |
|---|---|---|---|---|---|---|---|---|
| VI | methylisobutyl ketone | 1.0 BA | 2.0 | 15% | 85 C | 3 h | 90.1% | 99.8% |
| VII | cyclohexane | 2.0 BA | 2.0 | 11% | 77 C | 3 h | 96.0% | 99.8% |
| VIII | butyl acetate | 1.0 BA | 1.5 | 12% | 85 C | 2 h | 91.0% | 99.4% |
| IX | ethyl acetate/toluene: 1/3 | 2.0 BA | 1.5 | 12% | 86 C | 2 h | 96.0% | 99.3% |
| X | ethyl acetate/toluene: 1/3 | 1.5 AA | 1.0 | 14% | 84 C | 3.5 h | 96.7% | 99.8% |
| XI | ethyl acetate/toluene: 1/4 | 2.0 IBA | 1.0 | 11% | 80 C | 3 h | 92.4% | 99.8% |
| C | ethyl acetate: 1/3 toluene | 2.0 BA | 0 | 12% | 86 C | 3.5 h | 87.7% | 99.8% |
| D | methylisobutyl ketone | 0.1 BA | 1.0 | 15% | 70 C | 2.5 h | 93.7% | 50.5% |

Abbreviations:
AA = anisaldehyde
BA = benzaldehyde
IBA = isobutyraldehyde
* = optical purity of phenylglycine amide.HCL

EXAMPLE XII

In a reaction flask provided with a stirrer, a thermometer and a reflux cooler, 8.3 g (0.05 mole) D,L-p-hydroxyphenylglycine amide, 7.6 g (0.05 mole) L-mandelic acid, 150 ml toluene, 50 ml ethyl acetate, 6.0 ml (0.06 mole) benzaldehyde and 2.0 g (0.11 mole) water are stirred for 2.5 hours at a temperature of 85° C.

After cooling to 30° C. (¾ hour), the resulting diastereoisomeric salt of D-p-hydroxyphenylglycine amide and L-mandelic acid (DL salt) is filtered and washed on the glass filter with 5×20 ml ethyl acetate The yield of TLC pure DL salt amounts to 14.5 g, which corresponds to an efficiency of 91.2%. The specific rotation of the optically pure DL salt, after recrystallization from water, is: $[\alpha]^2_D = -8.1°$ (c=1.0; water) 1.6 g of the DL salt is dissolved in 20 ml water at 50° C., after which with stirring 1 ml 25 wt. % ammonia is added. After cooling to 20° C., filtration and washing of the resulting D-p-hydroxyphenylglycine amide crystals with, successively, 3×10 ml water and 3×10 ml methanol, the specific rotation of the TLC pure D-p-hydroxyphenylglycine amide (yield=0.8 g; efficiency=95.8%): $[\alpha]^{20}_D = -121°$ (c=1.0; 1.0 N acetic acid). The percentage of D-enantiomer is 99.8%.

EXAMPLE XIII

In a reaction flask provided with a stirrer, a thermometer and a reflux cooler, 33.2 g (0.20 mole) D,L-p-hydroxyphenylglycine amide, 30.5 g (0.20 mole) D-mandelic acid, 800 ml toluene, 200 ml ethyl acetate, 24 ml (0.24 mole) benzaldehyde and 8.0 g (0.44 mole) water are stirred for 2.5 hours at a temperature of 84° C. After cooling to 25° C. (1 hour), the resulting diastereoisomeric salt of L-p-hydroxyphenylglycine amide and D-mandelic acid (LD salt) is filtered and washed on the glass filter with 5×50 ml ethyl acetate. The yield of TLC pure LD salt amounts to 57.8 g, which corresponds to an efficiency of 90.9%.

The specific rotation of the optically pure LD salt (recrystallization from water) is: $[\alpha]^{20}_D = +8.0°$ (c=1.0;

water) 50.9 g (0.16 mole) of the LD salt is dissolved at 50° C. in 500 ml water, after which with stirring 25 ml (0.19 mole) 25 wt. % ammonia is added. After cooling to 30° C. the L-p-hydroxyphenylglycine amide crystals obtained are filtered and washed on the glass filter with 5×25 ml water. The yield of pure L-p-hydroxyphenylglycine amide after drying amounts to 25.1 g, corresponding to an efficiency of 94.3%.

The specific rotation of the L-p-hydroxyphenylglycine amide thus obtained is: $[\alpha]^{20}_D = +120.4°$ (c=1.0; 1.0 N acetic acid). The L-p-hydroxyphenylglycine amide (24.9 g=0.15 mole) is hydrolyzed to L-p-hydroxyphenylglycine with 33.3 ml 96 wt. % sulphuric acid (0.6 mole) in 57 ml water (3 hours; 90° C.). After neutralization to pH=4 by means of 90 ml 25 wt. % ammonia, the p-hydroxyphenylglycine is filtered at 20° C. and washed on the glass filter with 3×20 ml water. The yield of TLC pure L-p-hydroxyphenylglycine after drying amounts to 21.6 g, corresponding to an efficiency of 86.2%.

The specific rotation of the L-p-hydroxyphenylglycine is: $[\alpha]^{20}_D = +157.7°$ (c=1.0; 1.0 N hydrochloric acid).

EXAMPLE XIV-XVIII

In the same manner as in example XII, an asymmetric transformation of D,L-p-hydroxyphenylglycine amide is carried out with 1 equivalent D-mandelic acid. The results are given in table 2.

TABLE 2

| example | solvent | aldehyde (eq.) | water (eq.) | slurry concentr. | T | t | efficiency | selectivity |
|---|---|---|---|---|---|---|---|---|
| XIV | toluene/ethyl acetate = 3/1 | 0.5 BA | 2.0 | 13% | 85 C | 2.5 h | 94.3% | 78.8% |
| XV | toluene/ethyl acetate = 3/1 | 1.2 BA | 2.2 | 8% | 86 C | 1.5 h | 91.1% | 91.6% |
| XVI | toluene/tetra hydrofuran = 2/1 | 1.2 BA | 1.7 | 10% | 80 C | 5 h | 90.5% | 99.2% |
| XVII | toluene/ dioxane = 2/1 | 1.0 BA | 1.6 | 20% | 90 C | 4 h | 93.1% | 98.5% |
| XVIII | toluene/ dioxane = 5/1 | 2.0 CBA | 1.0 | 10% | 86 C | 2.5 h | 99.8% | |

Abbreviations:
BA = benzaldehyde
CBA = o-chlorobenzaldehyde
* = optical purity of p-hydroxyphenylglycine amide

EXAMPLES XIX AND XX AND COMPARATIVE EXPERIMENTS E AND F

In the same manner as in example XII, an asymmetric transformation of D,L-p-hydroxyphenylglycine amide is carried out with 1 equivalent L-mandelic acid, the quantities of water and benzaldehyde being varied. The results are given in table 3. Owing to the absence of water or aldehyde, the yield is considerably lower.

TABLE 3

| example | solvent | BA (eq.) | water (eq.) | slurry concentr. | T | t | efficiency |
|---|---|---|---|---|---|---|---|
| E | toluene/methyl tert.-butyl ether = 4/1 | 1.1 | 0 | 12% | 84 C | 3.5 h | 81.3% |
| XIX | toluene/methyl tert.-butyl ether = 4/1 | 1.1 | 1.1 | 12% | 84 C | 3.5 h | 92.5% |
| F | toluene/methyl acetate = 4/1 | 1 | 1.1 | 6% | 85 C | 2 h | 81.8% |
| XX | toluene/methyl acetate = 4/1 | 1.2 | 2.2 | 6% | 85 C | 2 h | 91.2% |

Abbreviation:
BA = benzaldehyde

EXAMPLE XXI

In a reaction flask provided with a stirrer, a thermometer and a reflux cooler, 23.7 g (0.10 mole) D,L-N-benzylidene methionine amide (SB of methionine amide and benzaldehyde), 12.9 g (0.10 mole) L-2-pyrrolidone-5-carboxylic acid, 200 ml ethyl acetate and 2.7 ml (0.15 mole) water are stirred for 2.5 hours at a temperature of 75° C. After cooling to 20° C. (0.5 hour), the resulting salt of L-methionine amide and L-2-pyrrolidone-5-carboxylic acid (LL salt) is filtered and washed on the glass filter with 4×25 ml ethyl acetate. The yield of TLC pure LL salt amounts to 21.2 g, which corresponds to an efficiency of 73.6%. 2.8 g (0.01 mole) of the LL salt is dissolved in a mixture of 3 ml water and 2 ml 12 N hydrochloric acid. After addition of 60 ml acetone to this solution, the L-methionine amide.HCl salt is isolated through filtration.

The specific rotation of the TLC pure L-methionine amide.HCl salt is: $[\alpha]^{20}_D = +17.9°$ (c=1.0; water) Selectivity: 99.2% L enantiomer.

EXAMPLE XXII

In a reaction flask provided with a stirrer, a thermometer and a reflux cooler, 10.7 g (0.04 mole) D,L-benzylidene homophenylalanine amide, 10.7 g (0.04 mole) L-Z-aspartic acid (L-N-(carbobenzoxy)aspartic acid) 110 ml MIBK and 1.5 g (0.08 mole) water are stirred for 5 hours at a temperature of 80° C. The resulting salt of D-homo-phenylalanine amide and L-Z-aspartic acid (DL-salt) is filtered and washed on the gloss filter with 2×25 mol MIBK. The yield of TLC pure DL-salt amounts to 9.46 g, which corresponds to an efficiency of 53%. 5 g (0.01 mole) of the DL-salt is split in a mixture of 100 ml water and 3.7 ml 6 N hydrochloric acid, in D-homophenylalanine amide.HCl salt L-Z-aspartic acid, which is extracted with ethylacetate. The D-homophenylalanine amide.HCl present in the water layer is hydrolyzed with 6 N hydrochloric acid at 80° C. into D-homophenylalanine. After neutralization and filtration, in order to remove the salts present, and after drying, a specific rotation of the TLC pure D-homophenylalanine is measured.

$[\alpha]^{20}_D = -29.2°$ (c=1; 1NHCl).
$[\alpha]^{20}_{D,lit} = -46.3°$.
Selectivity: 81.5% D enantiomer.

I claim:

1. Process for the preparation of an optically active amino acid amide comprising the steps of:
   (a) (i) mixing together a mixture of corresponding Schiff bases of L-amino and D-amino acid amides selected from the group consisting of phenylglycine amide, p-hydroxyphenylglycine amide, methionine amide, and homophenylalanine amide, a solvent, an optically active carboxylic acid selected from the group consisting of mandelic acid, 2-pyrrolidone-5-carboxylic acid and Z-aspartic acid, and water, wherein at least 1 equivalent of water is added relative to the quantity of said Schiff base, whereby the salt of said amino acid amide and said carboxylic acid is obtained, or (ii) mixing together a mixture of corresponding L-amino and D-amino acid amides selected from the group consisting of phenylglycine amide, p-hydroxyphenylglycine amide, methionine amide, and homophenylalanine amide, an aldehyde, a solvent and water, wherein the quantity of said aldehyde is 0.5–4 equivalents relative to the quantity of said amino acid amide, whereby the salt of said amino acid amide and said carboxylic acid is obtained;
   (b) separating, from the mixture resulting from step (a), a fraction consisting essentially of one of the diastereoisomers of said salt; and
   (c) converting the thus separated diastereoisomer of said salt into the corresponding amino acid amide.

2. Process according to claim 1, wherein said amino acid amide is phenylglycine amide and said optically active carboxylic acid is mandelic acid.

3. Process according to claim 1, wherein said amino acid amide is p-hydroxyphenylglycine amide and said optically active carboxylic acid is mandelic acid.

4. Process according to claim 1, wherein said amino acid amide is methionine amide and said optically active carboxylic acid is 2-pyrrolidone-5-carboxylic acid.

5. Process according to claim 1, wherein said amino acid amide is homophenylalanine amide and said optically active carboxylic acid is Z-aspartic acid.

6. Process according to claim 1, wherein step (a) (ii) the quantity of water is 0.5–3 equivalents relative to the quantity of amino acid amide.

7. Process according to claim 1, wherein step (a) (ii) the quantity of aldehyde is 1–2 equivalents relative to the quantity of amino acid amide.

8. Process according to claim 1, wherein said water is added prior to the reaction between said Schiff based or said amino acid amide and said carboxylic acid.

9. Process according to claim 1, wherein the carboxylic acid is used in equimolar quantities relative to said Schiff base or said amino acid amide.

10. Process according to claim 1, wherein said steps are carried out at a pressure of 0.01–1MPa and at a temperature of 70°–120° C., for approximately 1–8 hours.

11. Process according to claim 1, wherein the conversion into the salt of said amino acid amide and said carboxylic acid takes place at a temperature between 75° and 100° C.

12. Process for the preparation of optically active amino acids in which the salt of an amino acid amide and an optically active carboxylic acid, obtained by the process of claim 1, is treated with a mineral acid before separation from the reaction mixture.

13. Process for the preparation of an optically active amino acid amide comprising the steps of:
   i) mixing together a mixture of corresponding Schiff bases of L-amino and D-amino acid amides selected from the group consisting of phenylglycine amide, p-hydroxyphenylglycine amide, methionine amide, and homophenylalanine amide, a solvent, an optically active carboxylic acid selected from the group consisting of mandelic acid, 2-pyrrolidone-5-carboxylic acid and Z-aspartic acid, and water, wherein at least 1 equivalent of water is added relative to the quantity of said Schiff base, thereby converting the resulting mixture, in whole or in part, into the salt of said amino acid amide and said carboxylic acid;
   ii) separating, from said resulting mixture, a fraction consisting essentially of one of the diastereoisomers of said salt; and
   iii) converting said one diastereoisomer of said salt into the corresponding amino acid amide.

14. Process according to claim 13, wherein said water is added prior to the reaction between said Schiff base and said carboxylic acid.

15. Process according to claim 13, wherein the carboxylic acid is used in equimolar quantities relative to said Schiff base.

16. Process according to claim 13, wherein said steps are carried out at a pressure of 0.01–1 MPa and at a temperature of 70°–120° C., for approximately 1–8 hours.

17. Process according to claim 13, wherein the conversion into the salt of said amino acid amide and said carboxylic acid takes place at a temperature between 75° and 100° C.

18. Process for the preparation of optically active amino acids in which the salt of an amino acid amide and an optically active carboxylic acid, obtained by the process of claim 13, is treated with a mineral acid before separation from the reaction mixture.

19. Process for the preparation of an optically active amino acid amide comprising the steps of:
   (a) mixing together a mixture of corresponding L-amino and D-amino acid amides selected from the group consisting of phenylglycine amide, p-hydroxyphenylglycine amide, methionine amide, and homophenylalanine amide, an aldehyde, a solvent and water, wherein the quantity of said aldehyde is 0.5–4 equivalents relative to the quantity of said amino acid amide, whereby the salt of said amino acid amide and said carboxylic acid is obtained;
   (b) separating, from the mixture resulting from step (a), a fraction consisting essentially of one of the diastereoisomers of said salt; and
   (c) converting the thus separated diastereoisomer of said salt into the corresponding amino acid amide.

20. Process according to claim 19, wherein the quantity of water is 0.5-3 equivalents relative to the quantity of amino acid amide.

21. Process according to claim 19, wherein the quantity of aldehyde is 1-2 equivalents relative to the quantity of amino acid amide.

22. Process according to claim 19, wherein said water is added prior to the reaction between said amino acid amide and said carboxylic acid.

23. Process according to claim 19, wherein the carboxylic acid is used in equimolar quantities relative to said said amino acid amide.

24. Process according to claim 19, wherein said steps are carried out at a pressure of 0.01-1 MPa and at a temperature of 70°-120° C., for approximately 1-8 hours.

25. Process according to claim 19, wherein the conversation into the salt of said amino acid amide and said carboxylic acid takes place at a temperature between 75° and 100° C.

26. Process for the preparation of optically active amino acids in which the salt of an amino acid amide and an optically active carboxylic acid, obtained by the process of claim 19, is treated with a mineral acid before separation from the reaction mixture.

* * * * *